United States Patent [19]
Tsuchiya et al.

[11] Patent Number: 5,591,577
[45] Date of Patent: Jan. 7, 1997

[54] MOBILE GENETIC ELEMENT ORIGINATED FROM BREVIBACTERIUM STRAIN

[75] Inventors: Makoto Tsuchiya; Mika Moriya; Kiyoshi Miwa, all of Kawasaki, Japan

[73] Assignee: Ajinomoto Co., Inc., Tokyo, Japan

[21] Appl. No.: 146,010

[22] PCT Filed: Mar. 11, 1993

[86] PCT No.: PCT/JP93/00300
  § 371 Date: May 20, 1994
  § 102(e) Date: May 20, 1994

[87] PCT Pub. No.: WO93/18151
  PCT Pub. Date: Sep. 16, 1993

[30]  Foreign Application Priority Data

Mar. 11, 1992 [JP] Japan .......................... 4-52694

[51] Int. Cl.$^6$ .......................... C12Q 1/68; C12N 15/64; C12N 15/77; C12N 15/52
[52] U.S. Cl. .......................... 435/6; 435/172.3; 435/320.1; 536/23.2
[58] Field of Search .......................... 435/320.1, 172.3, 435/6, 252.3; 536/23.2, 23.5

[56]  References Cited
  FOREIGN PATENT DOCUMENTS

| | | |
|---|---|---|
| 0215388 | 3/1987 | European Pat. Off. . |
| 0252558 | 1/1988 | European Pat. Off. . |
| 0445385 | 9/1991 | European Pat. Off. . |
| WO92/02627 | 2/1992 | WIPO . |

OTHER PUBLICATIONS

Tsuchiya et al., *Bio/Technology*, vol. 6, 1988, pp. 428–430.

*Primary Examiner*—James S. Ketter
*Attorney, Agent, or Firm*—Oblon, Spivak, McClelland, Maier & Neustadt, P.C.

[57]  ABSTRACT

A DNA fragment which contains a mobile genetic element originated from a strain of the genus Brevibacterium is obtained, and a gene is transferred into the chromosomal DNA of the strain making use of the DNA fragment.

This invention provides a DNA fragment which contains a mobile genetic element originated from a strain of the genus Brevibacterium and a process for obtaining the DNA fragment, and a process for transferring a gene into the chromosomal DNA of the strain making use of the DNA fragment and a plasmid vector for use in the gene transfer process.

15 Claims, 3 Drawing Sheets

5,591,577

MOBILE GENETIC ELEMENT ORIGINATED FROM BREVIBACTERIUM STRAIN

TECHNICAL FIELD

This invention relates to a DNA fragment containing a mobile genetic element originated from a strain belonging to the genus Brevibacterium and a process for obtaining said DNA fragment, to a plasmid vector constructed using said DNA fragment and a process for transferring a gene into chromosome making use of said vector and to a strain of Brevibacterium obtained by said process, where said mobile genetic element is an essential factor for the chromosome engineering-aided improvement of Brevibacterium strains which are important in the amino acid industry.

BACKGROUND ART

Intensive studies have been carried out in the prior art on the breeding and improvement of strains of the genus Brevibacterium in order to achieve efficient production of amino acids. As a means for use in the breeding, a large number of genetic engineering techniques have been reported. Gene manipulation techniques for use in the breeding of strains belonging to the genus Brevibacterium have been developed making use of plasmid and phage systems, such as establishment of protoplast transformation methods (Katsumata, R., Ozaki, A., Oka, T. and Furuya, A.: *J. Bacteriol.* 159 (1984) 306–311, Santamaria, R. I., Gil, J. A. and Martin, J. F.: *J. Bacteriol.* 161 (1985) 463–467), development of various vectors (Miwa, K., Matsui, K. , Terabe, M., Nakamori, S., Sano, K. and Momose, H.: *Agric. Biol. Chem.* 48 (1984) 2901–2903, Katsumata, R., Ozaki, A., Oka, T. and Furuya, A.: *J. Bacteriol.* 159 (1984) 306–311, Santamaria, R., Gil, J. A., Mesas, J. M. and Martin, J. F.: *J. Gen. Microbiol.* 130 (1984) 2237–2246, Patek, M., Nesvera, J. and Hochmannova, J.: *Appl. Microbiol. Biotechnol.,* 31 (1989) 65–69, Yeh, P., Oreglia, J., Prevotos, F. and Scicard, A. M.: *Gene* 47 (1986) 301–306), development of gene expression controlling method (Tsuchiya, M. and Morinaga, Y.: *Bio/Technology* 6 (1988) 428–430) and development of cosmids (Miwa, K. , Matsui, K. , Terabe, M., Ito, K., Ishida, M., Takagi, H., Nakamori, S. and Sano, K.: *Gene* 39 (1985) 281–286). Also reported are cloning of genes making use of such systems (Melumbres, M., Mateos, L. M. , Guerrero, C. and Martin, J. F.: *Nucleic Acids Res.,* 16 (1988) 9859, Mateos, L. M., Del, R. G., Aguilar, A. and Martin, J. F.: *Nucleic Acids Res.,* 15 (1987) 10598, Matsui, K., Miwa, K. and Sano, K.: *Agric. Biol . Chem.* 52 (1988) 525–531, Mateos, L. M., Del, R. G., Auilar, A. and Martin, J. F.: *Nucleic Acids Res.,* 15 (1987) 3922, Matsui, K., Sano, K. and Ohtsubo, E.: *Nucleic Acids Res.,* 14 (1986) 10113–10114, Peoples, O. P., Liebl, W., Bodis, M., Maeng, P. J., Follettie, M. T., Archer, J. A. and Shinskey, A. J.: *Mol. Microbiol.,* 2 (1988) 63–72, Eikmanns, B. J., Follettie, M. T., Griot, M. U., Martin, U. and Shinskey, A. J.: *Mol. Gen. Genet.,* 218 (1989) 330–339, O'Regan, M., Thierbach, G., Bachmann, B., VGilleval Lepage, P., Viret, J. F. and Lemoine, Y.: *Gene* 77 (1989) 237–251, Follettie, M. T. and Shinskey, A. J.: *J. Bacteriol.,* 167 (1986) 695–702) and yield improvement of various amino acids (Sano, K., Ito, K., Miwa, K. and Nakamori, S.: *Agric. Biol. Chem.,* 51 (1987) 597–599).

However, there are no reports on mobile genetic elements originated from strains belonging to the genus Brevibacterium.

Mobile genetic element is a DNA fragment which can move on the chromosome and its existence is known in a large variety of organisms ranging from procaryotic to eucaryotic organisms, especially in detail in corn, Drosophila, yeast and the like as eucaryotic organisms and *Escherichia coli* and the like as procaryotic organisms (*Mobile DNA*, American Society for Microbiology, Washington D.C. (1989)). Also, Japanese Patent Application Laying Open (Kokai) No. 63-24889 discloses a mobile genetic element originated from *Corynebacterium diphtheriae* and European Patent Application 0,445,385 A discloses a transposon originated from a bacterium belonging to the genus Corynebacterium.

Mobile genetic elements of bacterial origins are divided into insertion sequence and transposon. Insertion sequence is a DNA fragment having a size of from 760 bp to 2000 bp, with its both termini having inverted repeat sequences and its inner region encoding transposase which is an enzyme necessary for its moving. Transposon is a mobile genetic element having a gene which does not take part directly in the transfer, such as a drug resistant gene, and is present in a form in which said gene is interposed between two insertion sequences or inserted into an insertion sequence. As a characteristic feature common to insertion sequence and transposon, it is known that duplication of a nucleotide sequence of about 10 bp can be found in the periphery of a region where either of them is inserted (*Mobile Genetic Elements*, Academic Press, New York (1983) p159–221).

Some of the currently known mobile genetic elements, such as *Escherichia coli* transposons Tn 10 and Tn 5 and Mu phage, are markedly useful in genetic engineering. Examples of such use include gene disruption in which expression of a chromosomal gene is inhibited by inserting a transposon into the gene, gene expression in which a transposon having a promoter sequence inserted therein is transferred on a chromosome thereby effecting expression of its downstream sequence, and gene transfer in which a new gene is transferred into a chromosome by inserting the new gene into a transposon and effecting its transfer on the chromosome (*Mobile DNA*, American Society for Microbiology, Washington D.C. (1989) 879–925).

An object of the present invention is to obtain a DNA fragment containing a mobile genetic element originated from a strain belonging to the genus Brevibacterium, which is essential for the chromosome engineering-aided improvement of Brevibacterium strains that are important in the amino acid industry. Its another object is to provide a process for obtaining said mobile genetic element and establish a process for transferring a gene into chromosomal DNA making use of said mobile genetic element.

DISCLOSURE OF THE INVENTION

With the aim of achieving the aforementioned objects, the inventors of the present invention have conducted intensive studies and, as the results, a DNA fragment containing an active mobile genetic element was obtained from the chromosome of a strain belonging to the genus Brevibacterium and, after cloning, its nucleotide sequence was determined. A gene transfer process was also established making use of said mobile genetic element. Nucleotide sequence duplication was observed on the chromosome at the periphery of a region where said mobile genetic element was inserted (target site), and the presence of an inverted repeat sequence which can be found commonly at the termini of mobile genetic elements of other organisms was also confirmed.

Accordingly, the present invention relates to a DNA fragment which contains a mobile genetic element originated from a strain belonging to the genus Brevibacterium.

The present invention also relates to a process for obtaining the just described DNA fragment which comprises the steps of 1) carrying out transformation by introducing a plasmid pEC701 into a strain belonging to the genus Brevibacterium, 2) selecting a strain transformed with pEC701 using kanamycin resistance as a marker, 3) inoculating the Brevibacterium strain having the plasmid pEC701 onto an IPTG-containing agar plate to select a strain grown on the medium, 4) analyzing nucleotide sequence of a CAT structural gene or expression controlling sequence of a plasmid contained in the selected strain and 5) finding a sequence inserted into said sequence, and to another process for obtaining the just described DNA fragment which comprises the steps of 1) carrying out transformation by introducing a plasmid pEC901 into a strain belonging to the genus Brevibacterium, 2) selecting a strain transformed with pEC901 using kanamycin resistance as a marker, 3) culturing the Brevibacterium strain containing pEC901 at 30° C. to select a strain capable of expressing chloramphenicol resistance even under a condition of 30° C., 4) analyzing nucleotide sequence of a cI repressor gene of a plasmid contained in the selected strain and 5) finding a sequence inserted into said sequence.

Also, with the aim of achieving the aforementioned objects, the inventors of the present invention have continued intensive studies and found as the results that multiple copies of an exogenous gene can be introduced into the chromosome of a strain belonging to the genus Brevibacterium, by means of homologous recombination making use of an insertion sequence which exists in multiple copies on the chromosomal DNA of the Brevibacterium strain, thus resulting in the accomplishment of the present invention.

Accordingly, the present invention relates to a process for introducing a gene of Brevibacterium strains, such as a gene encoding an enzyme engaged in an amino acid biosynthesis, into the chromosomal DNA of a strain belonging to the genus Brevibacterium, making use of a plasmid vector containing an insertion sequence of the Brevibacterium strain, and to a Brevibacterium strain obtained by said process. Since the insertion sequence exists in multiple copies on the chromosomal DNA, this is a useful sequence which renders possible multicopy transfer of a useful gene of interest onto the chromosome by its homologous recombination.

Also, as a result of the intensive studies, it was found that, when a transposon-like sequence was artificially constructed from an insertion sequence in the chromosomal DNA of a strain belonging to the genus Brevibacterium, the transposon-like sequence was capable of showing similar function as a transposon, thus resulting in the accomplishment of the present invention.

Accordingly, the present invention relates to a process for introducing a gene of Brevibacterium strains, such as an amino acid synthetase gene, into the chromosomal DNA of a strain belonging to the genus Brevibacterium, making use of a plasmid vector containing a transposon-like sequence constructed using an insertion sequence in the chromosomal DNA of the strain of Brevibacterium, and to a Brevibacterium strain obtained by said process.

Taking note of a fact that the known transposon exerts its transfer action by forming a structure in which a gene unrelated to the transfer action is interposed between two identical insertion sequences, the inventors of the present invention have constructed a sequence having such a structure that a gene unrelated to the transfer action is interposed between two insertion sequences originated from the chromosomal DNA of a strain belonging to the genus Brevibacterium, and found that the thus constructed sequence can exert a transfer action as a transposon, thus resulting in the accomplishment of the present invention. The following describes the present invention in detail.

According to the present invention, the strain belonging to the genus Brevibacterium from which a DNA fragment containing a mobile genetic element is derived is an aerobic gram-positive bacillus as disclosed in *Bergey's Manual of Determinative Bacteriology*, 8th ed., page 599 (1974). A preferred example of the strain is *Brevibacterium lactofermentum* AJ2256.

Introduction of a plasmid into the aforementioned strain of the genus Brevibacterium may be effected by commonly used means such as protoplast transformation (Gene, 39 (1985) 281–286), electroporation (*Bio/Technology*, 7 (1989) 1067–1070) and the like. Introduction of a recombinant plasmid having a DNA fragment that contains a mobile genetic element can also be made by the same means.

Culturing of a transformant thus obtained may be carried out by any of the usually used methods and conditions.

The mobile genetic element according to the present invention is a DNA fragment which can move on a chromosome. In addition, both termini of the mobile genetic element are possessed of inverted repeat sequences.

The DNA fragment of the present invention containing the mobile genetic element originated from a Brevibacterium strain can be obtained in the following manner.

Transformation is carried out by introducing a plasmid pEC701 into a strain belonging to the genus Brevibacterium. A strain transformed with pEC701 can be selected using kanamycin resistance as a marker.

Next, the Brevibacterium strain having the plasmid pEC701 is inoculated onto an IPTG-containing agar plate to select a strain grown on the medium. As shown in FIG. 1, pEC701 has a structural gene of chloramphenicol acetyltransferase (CAT) which is regulated by tac promoter. Because of this, a pEC701-containing strain of Brevibacterium selected using kanamycin resistance as a marker induces and expresses CAT gene by the addition of IPTG (isopropyl-β-thiogalactoside) (*Bio/Technology*, 6 (1988) 428–430). However, a phenomenon of simultaneous growth termination is also known. In consequence, a strain capable of growing on this medium does not have the ability to induce and express CAT gene by IPTG. The cause of this may be due to the insertion of the mobile genetic element into CAT structural gene or into a sequence which controls expression of CAT structural gene such as promoter and terminator.

By analyzing the thus selected strain, the mobile genetic element inserted into the CAT structural gene or expression controlling sequence can be found.

The DNA fragment of the present invention containing the mobile genetic element originated from a Brevibacterium strain can also be obtained in the following manner.

Transformation is carried out by introducing a plasmid pEC901 into a strain belonging to the genus Brevibacterium. A strain transformed with pEC901 can be selected using kanamycin resistance as a marker.

Next, the thus selected Brevibacterium strain having the plasmid pEC901 is cultured at 30° C. to select a strain capable of expressing chloramphenicol resistance even under a condition of 30° C. As shown in FIG. 2, pEC901 has a gene coding for a temperature sensitive cI repressor and a CAT gene which is regulated by $P_R P_L$ promoter. Because of this, a pEC901containing strain of Brevibacterium cannot grow in the presence of chloramphenicol when cultured at 30° C. due to the inhibition of the CAT gene expression. However, when cultured at 40° C., the cI repressor is inactivated and expression of the CAT gene is induced, thereby making the cells into chloramphenicol-resistant form (Bio/Technology, 6 (1988) 428–430). In consequence, it seems that, in a strain capable of growing at 30° C., the mobile genetic element is inserted into the cI repressor gene or expression of the cI repressor is inhibited by the insertion of the mobile genetic element.

By analyzing the thus selected strain, the mobile genetic element inserted into the cI repressor gene can be found.

Nucleotide sequence of the thus obtained mobile genetic element can be determined by the usual way such as dideoxy method and the like. By determining the nucleotide sequence, the presence of inverted repeat sequences on its both termini and duplication of sequences as the insertion target, both being known in mobile genetic elements of other biological species, can be observed.

Nucleotide sequences of three mobile genetic elements obtained by the aforementioned process are shown in the Sequence ID Nos. 1, 3 and 4 in the Sequence Listing attached hereto. The sequences shown herein should not necessarily be considered in the strict sense, and their derivatives resulting from addition, deletion or substitution of some bases which do not take part directly in the moving function of the mobile genetic elements may also be included in the inventive mobile genetic elements.

The process of the present invention for the transfer of a gene into the chromosomal DNA of a strain belonging to the genus Brevibacterium by means of homologous recombination making use of an insertion sequence originated from the Brevibacterium strain is carried out in the following manner.

Firstly, an insertion sequence obtained from a strain belonging to the genus Brevibacterium is cloned into a plasmid vector such as a plasmid pHSC4 (French Patent Application 2,667,875A) whose replication function in the Brevibacterium strain is temperature sensitive. An *Escherichia coli* strain, AJ12571, containing the plasmid pHSC4 has been deposited as FERM BP-3524 in National Institute of Bioscience and Human Technology, Agency of Industrial Science and Technology, the Ministry of International Trade and Industry. Next, a gene of interest to be introduced into the chromosomal DNA, such as a drug resistance gene or a gene encoding an enzyme engaged in an amino acid biosynthesis, is inserted into the insertion sequence-inserted plasmid vector in such a manner that the insertion sequence is not cut off. This insertion step is not required when the plasmid vector already contains such a gene. In this instance, insertion of the insertion sequence and the gene to be introduced may be carried out in either order.

When the Brevibacterium strain was transformed with the thus prepared plasmid, insertion of the introduced gene into the chromosome and its high level expression were observed. These results support that the insertion sequence of the present invention is useful in a process in which useful genes related to the amino acid production and the like are introduced into chromosomes and expressed at a high level thereby effecting large scale production of useful substances such as amino acids and the like.

The transposon-like sequence-aided transfer of a gene into the chromosomal DNA of a strain belonging to the genus Brevibacterium making use of the Brevibacterium strain-originated insertion sequence of the present invention is carried out in the following manner.

Firstly, the insertion sequence obtained from the strain of Brevibacterium is cloned into a plasmid vector such as the plasmid pHSC4 whose replication function in the Brevibacterium strain is temperature sensitive. Next, a gene which is not concerned in the transfer function of the insertion sequence, such as a drug resistance gene or a gene encoding an enzyme engaged in an amino acid biosynthesis, is inserted into the insertion sequence-inserted plasmid vector. This insertion step is not required when the plasmid vector already contains such a gene. Thereafter, an insertion sequence having almost the same nucleotide sequence as that of the previously introduced insertion sequence is inserted into the thus obtained plasmid containing one insertion sequence and a gene unrelated to the transfer function of the sequence. In this case, insertion of the second insertion sequence is carried out by selecting a proper cloning site so that the transfer-unrelated gene is interposed between the two insertion sequences. In this way, a transposon-like sequence is prepared making use of these insertion sequences. In this instance, the two insertion sequences and the gene of interest to be introduced into the chromosome may also be inserted into the plasmid in other orders than the above. In addition, relative direction of the two insertion sequences is not particularly limited.

The plasmid vector containing the thus prepared transposon-like sequence is introduced into a strain of Brevibacterium which already contains a plasmid vector as the transfer target of the transposon-like sequence, thereby making a coexisting state of the two plasmids. The plasmid vector containing the transposon-like sequence is a plasmid which has a temperature sensitive replication origin. Selective segregation of the plasmid containing the transposon-like sequence can be made by culturing the Brevibacterium strain which simultaneously contains the transposon-like sequence-containing plasmid and the the transfer target plasmid at such a temperature that only the plasmid having the temperature sensitive replication origin cannot be replicated. A strain capable of expressing the gene inserted into the transposon-like sequence, obtained by culturing the strain simultaneously containing the two plasmids at such a temperature that the plasmid containing the transposon-like sequence cannot be replicated, could be regarded as a strain in which the gene to be introduced is inserted into the chromosomal DNA or the plasmid. Actually, when the Brevibacterium strain which simultaneously contains the transposon-like sequence-containing plasmid and the transfer target plasmid was cultured at such a temperature that the transposon-like sequence-containing plasmid cannot be replicated, strains capable of expressing the gene contained in the transposon-like sequence were obtained. By extracting plasmids from these strains and analyzing their sizes, transfer of the transposon-like sequence to the transfer target plasmid was found. As a matter of course, the chromosomal DNA could also be regarded as the transfer target in addition to the plasmid. These results support that the transposon-like sequence of the present invention is a useful tool by which useful genes related to the amino acid production and the like can be introduced into chromosomes thereby rendering possible large scale production of useful substances such as amino acids and the like.

NPT is a neomycin phosphotransferase gene. In this instance, a portion of the sequence of a chloramphenicol resistance gene of pEC701-IS14 origin is adhered to both termini of IS714.

Figure 4:
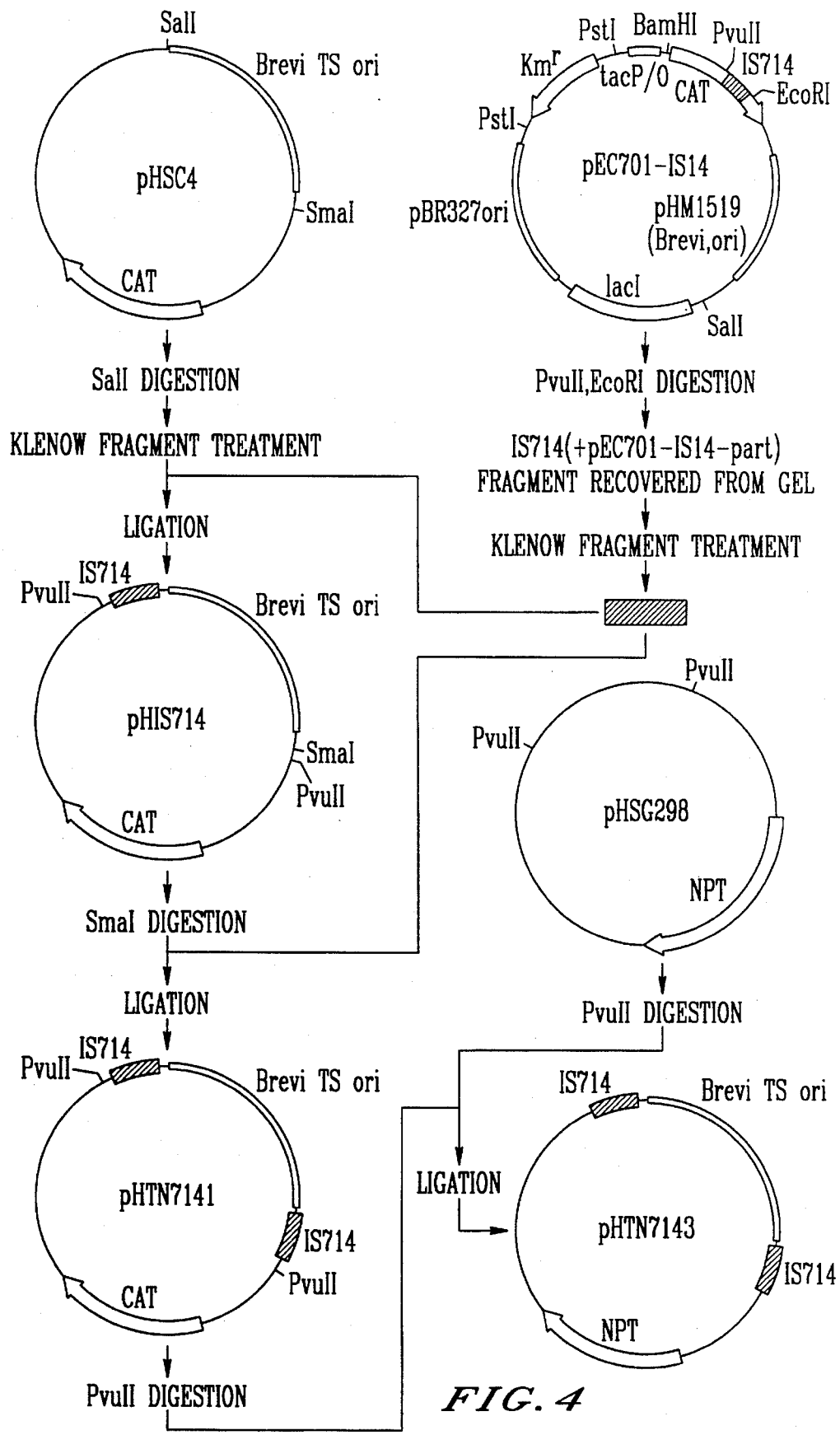

FIG. 4 is a schematic illustration showing a procedure for the construction of a plasmid pHTN7143 having a transposon-like sequence making use of the insertion sequence IS714. In this drawing, Brevi TS Ori is a pHSC4-originated temperature sensitive replication origin in Brevibacterium.

NPT is a neomycin phosphotransferase gene.

EXAMPLES

The following examples are provided to further illustrate the present invention.

(Preparation of IS714 and IS719)

Plasmid pEC701 was introduced into *Brevibacterium lactofermentum* AJ2256. The resulting strain was cultured overnight at 30° C. on a shaker using a CM2G medium (10 g of yeast extract, 10 g of tryptone, 5 g of glucose and 5 g of NaCl dissolved in 1 liter of water) which has been supplemented with 25 µg/ml of kanamycin, and the thus obtained culture broth was diluted and applied to CM2G agar medium supplemented with 0.2 mM of IPTG and 25 µg/ml of kanamycin. When plasmids were extracted from colonies grown on the agar medium and analyzed for their structures by restriction enzyme digestion, two plasmids having larger molecular weights than that of pEC701 were obtained. In both of these plasmids, insertion of a sequence into the chloramphenicol acetyltransferase gene was found. The sequences inserted into these two plasmids were respectively named IS714 and IS719, and the plasmids resulting from the insertion of IS714 into pEC701 and of IS719 into pEC701 were respectively named pEC701-IS14 and pEC701-IS19. *Brevibacterium lactofermentum* AJ12684 containing the plasmid pEC701-IS14 and *Brevibacterium lactofermentum* AJ12685 containing the plasmid pEC701-19 have been deposited, respectively as FERM BP-4232 and FERM BP-4233, in National Institute of Bioscience and Human Technology, Agency of Industrial Science and Technology, the Ministry of International Trade and Industry. Nucleotide sequences of both terminal regions of the insertion sequences in these plasmids were determined by the dideoxy method. Nucleotide sequences of IS714 and IS719 are shown in Sequence ID Nos. 1 and 3, respectively. In IS714, a sequence GGCCCTTCCG GTTTT (Sequence ID No. 5) was presented on its 5' side, and a sequence AAAAACGGAA GAGCC (Sequence ID No. 6) on its 3' side, thus forming inverted repeat sequences. Also, duplication of 8 bp ATATTACG was found around the insertion region in the chloramphenicol acetyltransferase gene used as the target. In IS719, a sequence GGCCCTTCCG GTTTT (Sequence ID No. 5) was presented on its 5' side, and a sequence AAAACAGGAA GAGCC (Sequence ID No. 7) on its 3' side, thus forming inverted repeat sequences. Also, duplication of 8 bp CCTTTATT was found around the insertion region in the chloramphenicol acetyltransferase gene used as the target. On the basis of these facts, the inserted sequence thus obtained was determined to be an insertion sequence whose existence in Brevibacterium was confirmed for the first time by the present invention.

As a result of the analysis of the nucleotide sequence shown in Sequence ID No. 1, an open reading frame was found. Amino acid sequence of a protein encoded thereby is shown in Sequence ID No. 2. This protein is considered to be transposase.

(Preparation of IS903)

Plasmid pEC901 was introduced into *Brevibacterium lactofermentum* AJ2256. The resulting strain was cultured overnight at 30° C. on a shaker using CM2G medium (10 g of yeast extract, 10 g of tryptone, 5 g of glucose and 5 g of NaCl dissolved in 1 liter of H₂O) which has been supplemented with 25 µg/ml of kanamycin, and the thus obtained culture broth was diluted, applied to CM2G agar medium supplemented with 3 µg/ml of chloramphenicol and 25 µg/ml of kanamycin and then cultured at 30° C. When plasmids were extracted from colonies grown on the agar medium and analyzed for their structures by restriction enzyme digestion, a plasmid having a larger molecular weight than that of pEC901 was obtained. In this plasmid, insertion of a sequence into the cI857 repressor-encoding gene was found. The sequence inserted into this plasmid was named IS903, and the plasmid resulting from the insertion of IS903 into pEC901 was named pEC901-IS03. *Brevibacterium lactofermentum* AJ12686 containing the plasmid pEC901-IS03 has been deposited, as FERM BP-4234, in National Institute of Bioscience and Human Technology, Agency of Industrial Science and Technology, the Ministry of International Trade and Industry. Nucleotide sequences of both terminal regions of the insertion sequence in this plasmid was determined by the dideoxy method. Nucleotide sequence of IS903 is shown in Sequence ID No. 3. In IS903, a sequence GGGACTGACC CCTG (Sequence ID No. 8) was presented on its 5' side, and a sequence CGGGGGTCGG GCCC (Sequence ID No. 9) on its 3' side, thus forming inverted repeat sequences. Also, duplication of 3 bp CGT was found around the insertion region in the cI857 repressor gene used as the target. On the basis of these facts, the inserted sequence thus obtained was determined to be an insertion sequence whose existence in Brevibacterium was confirmed for the first time by the present invention.

(IS714-aided construction of vector for gene integration use)

Figure 1:
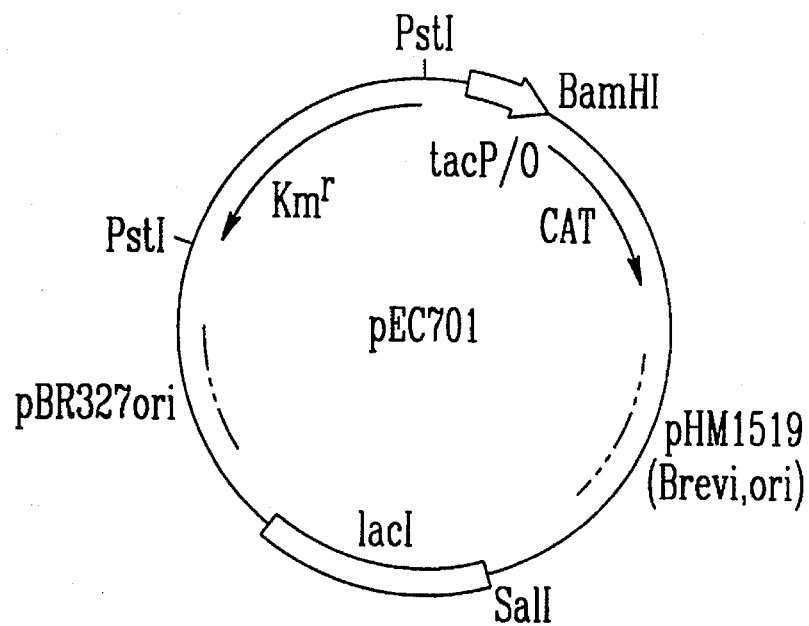
FIG. 1 is a schematic illustration showing the structure of pEC701.
Figure 2:
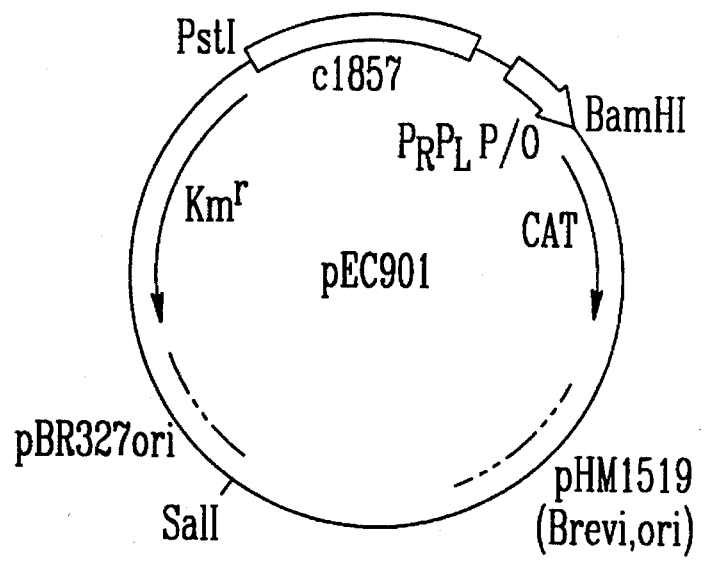
FIG. 2 is a schematic illustration showing the structure of pEC901.
Figure 3:
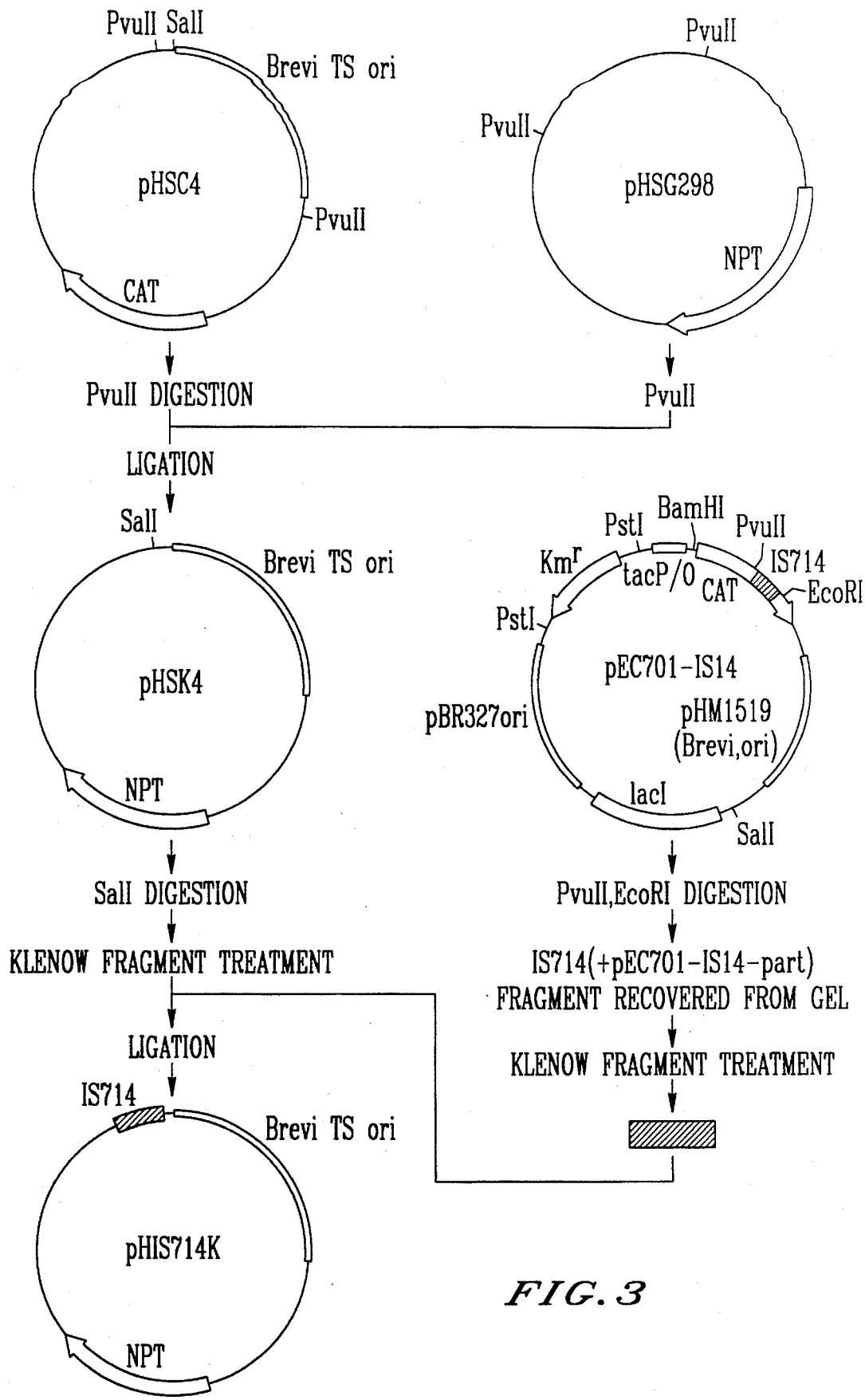
FIG. 3 is a schematic illustration showing a procedure for the construction of a plasmid pHIS714K for gene transfer use making use of an insertion sequence IS714. In this drawing, Brevi TS Ori is a pHSC4-originated temperature sensitive replication origin in Brevibacterium.

It is possible to cut out the temperature sensitive replication origin sequence in Brevibacterium by digesting the plasmid pHSC4 with restriction enzyme PvuII. On the other hand, it is possible to obtain a 2.6 kb fragment containing the neomycin phosphotransferase gene from a plasmid vector pHSG298 (*Gene*, 61 (1987) 63–74) by digesting it with restriction enzyme PvuII. Plasmids pHSC4 and pHSG298 were digested with restriction enzyme PvuII, subjected to ligation and then introduced into *Brevibacterium lactofermentum* AJ2256. A strain having a resistance against 25 µg/ml of kanamycin was selected from the resulting transformants, and a plasmid named pHSK4 was obtained from the strain. Separately from this, the plasmid pEC701-IS14 which contains the *Brevibacterium lactofermentum* AJ2256-originated insertion sequence, IS714, was digested with restriction enzymes PvuII and EcoRI to obtain an IS714-containing fragment of 1.6 kb. The IS714-containing fragment was inserted into a restriction enzyme SalI site located at a position unrelated to the replication of pHSK4. In this case, both fragments were treated with Klenow fragment to form blunt ends and then subjected to ligation to prepare a plasmid pHIS714K. Details of the above procedure are shown in FIG. 3. The plasmid pHIS714K contains IS714, neomycin phosphotransferase gene and pHSC4-originated sequence of the temperature sensitive replication origin in Brevibacterium. Also, as another plasmid for use in the gene transfer, pHSK4D was prepared by cloning a 3-deoxy-D-arabinohepturosonate-7-phosphate synthase gene originated from *Brevibacterium lactofermentum*.

(Gene integration into chromosome making use of IS714)

The thus prepared plasmid pHIS714K was transformed into *Brevibacterium lactofermentum* AJ2256. A transformant thus obtained was cultured overnight at 25° C. on a shaker using CM2G medium (10 g of yeast extract, 10 g of tryptone, 5 g of glucose and 5 g of NaCl dissolved in 1 liter of water) which has been supplemented with 25 μg/ml of kanamycin, and the thus obtained culture broth was diluted, applied to two CM2G agar medium plates respectively supplemented with 150 μg/ml and 200 μg/ml of kanamycin and then cultured at 30° C. Plasmids pHSK4 and pHSK4D were also subjected to transformation and culturing in the same manner. As the results, as shown in Table 1, significantly large number of resistant strains to 150 μg/ml and 200 μg/ml of kanamycin were generated from the transformant containing pHIS714K, in comparison with other transformants respectively containing the vector plasmid pHSK4 and the gene transfer vector pHSK4D which does not have the insertion sequence. Generation of these resistant strains to high concentration kanamycin is considered to be due to the insertion of a plurality of neomycin phosphotransferase gene into the chromosome caused by homologous recombination of the IS714 on pHIS714K with the sequence of IS714 which exists in plural numbers on the chromosome. On the contrary, since homologous recombination does not occur in the strain containing pHSK4 which has no sequences homologous to those on the chromosome, generation of high concentration kanamycin resistant strains did not occur after segregation of the plasmid. A 3-deoxy-D-arabinohepturosonate-7-phosphate synthase gene is inserted into pHSK4D. Though its homologous recombination seems to occur because of the presence of said gene on the chromosome, its copy number on the chromosome is only one, and, because of this, the neomycin phosphotransferase gene cannot be inserted in plural numbers into the chromosome thus resulting in the generation of no high concentration kanamycin resistant strains.

| Plasmid | Cells per plate | Km resistant strains | |
|---|---|---|---|
| | | Km concentration 150 g/ml | Km concentration 200 g/ml |
| pHSK4 | 3.07 × 10⁵ | 1 | 0 |
| pHSK4D | 3.03 × 10⁵ | 0 | 0 |
| pHIS714K | 3.30 × 10⁵ | 10 | 4 |

Km stands for kanamycin (Construction of transposon-like sequence making use of IS714)

Plasmid pEC701-IS14 which contains the *Brevibacterium lactofermentum* AJ2256-originated insertion sequence, IS714, was digested with restriction enzymes PvuII and EcoRI to obtain an IS714-containing fragment of 1.6 kb. The IS714-containing fragment was inserted into a restriction enzyme SalI site located at a position unrelated to the replication of a mutant type plasmid pHSC4 whose replication function has been changed into a temperature sensitive type. Both fragments were treated with Klenow fragment to form blunt ends and then subjected to ligation. Into the SmaI site of the thus prepared plasmid pHIS714 was inserted another IS714-containing fragment of 1.6 kb which has been obtained from the plasmid pEC701-IS14 by digesting it with restriction enzymes PvuII and EcoRI. Both fragments were treated with Klenow fragment to form blunt ends and then subjected to ligation to prepare pHTN7141. As a result of restriction enzyme digestion analysis, it was found that, in this plasmid pHTN7141, the IS714-containing fragments inserted into two different sites have the same orientation. It is possible to cut out the two IS714 sequences and the temperature sensitive replication origin sequence of pHSC4 in Brevibacterium by digesting the thus prepared plasmid pHTN7141 with restriction enzyme PvuII. On the other hand, since a plasmid vector pHSG298 (*Gene*, 61 (1987) 63–74) also has two restriction enzyme PvuII sites, it is possible to obtain a 2.3 kb fragment containing the neomycin phosphotransferase gene from this plasmid by digesting it with restriction enzyme PvuII. A small fragment obtained by digesting pHTN7141 with restriction enzyme PvuII and a large fragment obtained by digesting pHSG298 with restriction enzyme PvuII were subjected to ligation and introduced into *Brevibacterium lactofermentum* AJ2256. A strain having a resistance against 25 μg/ml of kanamycin was selected from the resulting transformants to isolate a plasmid named pHTN7143. Details of the above procedure are shown in FIG. 4. The plasmid pHTN7143 contains the neomycin phosphotransferase gene interposed between two IS714 sequences and pHSC4-originated sequence of the temperature sensitive replication origin in Brevibacterium. Many transposons have a structure in which a transfer-unrelated gene is interposed between two insertion sequences. *Brevibacterium lactofermentum* AJ12686 containing the plasmid pHTN7143 has been deposited in National Institute of Bioscience and Human Technology, Agency of Industrial Science and Technology, the Ministry of International Trade and Industry, and has been assigned the designation as FERM BP-4231.

(Transfer experiment of transposon-like sequence)

The thus prepared plasmid vector pHTN7143 containing the transposon-like sequence was introduced into *Brevibacterium lactofermentum* AJ2256, thereby allowing it to coexist with the strain's inherent plasmid vector pAJ43 which contains a chloramphenicol acetyltransferase (CAT) gene. A strain of *Brevibacterium lactofermentum* containing the plasmid pAJ43 has been deposited in National Institute of Bioscience and Human Technology, Agency of Industrial Science and Technology, the Ministry of International Trade and Industry, and has been assigned the designation as FERM BP-136. *Brevibacterium lactofermentum* AJ2256 which simultaneously contains plasmids pHTN7143 and pAJ43 was cultured overnight at 25° C. on a shaker using CM2G medium (10 g of yeast extract, 10 g of tryptone, 5 g of glucose and 5 g of NaCl dissolved in 1 liter of water) which has been supplemented with 25 μg/ml of kanamycin and 5 μg/ml of chloramphenicol, and the thus obtained culture broth was diluted, applied to CM2G agar medium supplemented with 25 μg/ml of kanamycin and 5 μg/ml of chloramphenicol and then cultured at 34° C. When plasmids were extracted from 100 strains isolated from colonies grown on the agar medium and their sizes were examined by electrophoresis, one of the strains was found to have a plasmid whose molecular weight is different from those of the plasmids pHTN7143 and pAJ43 but equal to the sum of the molecular weights of pAJ43 and the transposon-like sequence. When analyzed by restriction enzyme digestion, it was found that this plasmid was a product resulting from the insertion of the sequence on pHTN7143 into pAJ43. When nucleotide sequences around the connecting sites of the inserted fragment and pAJ43 in the thus insertion-received pAJ43 were determined by the dideoxy method, presence of sequences of both termini of the transposon-like sequence and duplication of 8 bp target sequence GGTTTACC of the insertion-received pAJ43 were confirmed. It was verified on the basis of these results that, when the transposon-like sequence is allowed to form a structure in which a transfer-unrelated gene (neomycin phosphotransferase gene) is interposed between two IS714 sequences, it exerts a transfer function like a transposon while keeping such a structure intact.

Industrial Applicability

The present invention provides a DNA fragment containing a mobile genetic element originated from a strain belonging to the genus Brevibacterium and a process for transferring a gene into chromosome making use of said DNA fragment. Being discovered for the first time in a Brevibacterium strain, said mobile genetic element has an important meaning for the gene manipulation of Brevibacterium strains.

---

We claim:

1. The DNA fragment of SEQ ID NO: 3, wherein said fragment consists of nucleotide sequence represented by the following formula:

```
GGCCCTTCCG  GTTTTGGGGT  ACATCACAGA
            ACCTGGGCTA  GCGGTGTAGA  CCCGAAAATA
AACGAGCCTT  TTGTCAGGGT  TAAGGTTTAG
            GTATCTAAGC  TAACCAAACA  CCAACAAAAG
GCTCTACCCA  TGAAGTCTAC  CGGCAACATC
            ATCGCTGACA  CCATCTGCCG  CACTGCGGAA
CTAGGACTCA  CCATCACCGG  CGCTTCCGAT
            GCAGGTGATT  ACACCCTGAT  CGAAGCAGAC
GCACTCGACT  ATACCTCCAC  CTGCCCAGAA
            TGCTTCCAAC  CTGGGGTGTT  TCGTCATCAC
ACCCACCGGA  TGCTCATTGA  TTTACCCATC
            GTCGGGTTTC  CCACCAAACT  GTTTATCCGT
CTACCTCGCT  ACCGCTGCAC  CAACCCGACA
            TGTAAGCAAA  AGTATTTCCA  AGCAGAACTA
AGCTGCGCTG  ACCACGGTAA  AAAGGTCACC
            CACCGGGTCA  CCCGCTGGAT  TTTGCAACGC
CTTGCTATTG  ACCGGATGAG  TGTTCACGCA
            ACTGCGAAAG  CACTTGGGCT  AGGGTGGGAT
TTAACCTGCC  AACTAGCCCT  CGATATGTGC
            CGTGAGCTGG  TCTATAACGA  TCCTCACCAT
CTTGATGGAG  TGTATGTCAT  TGGGGTGGAT
            GAGCATAAGT  GGTCACATAA  TAGGGCTAAG
CATGGTGATG  GGTTTGTCAC  CGTGATTGTC
            GATATGACCG  GGCATCGGTA  TGACTCACGG
TGTCCTGCC   CGGTTATTAGA TGTCGTCCCA
            GGTCGTAGTG  CTGATGCTTT  ACGGTCCTGG
CTTGGCTCCC  GCGGTGAACA  GTTCCGCAAT
            CAGATACGGA  TCGTGTCCAT  GGATGGATTC
CAAGGCTACG  CCACAGCAAG  TAAAGAACTC
            ATTCCTTCTG  CTCGTCGCGT  GATGGATCCA
TTCCATGTTG  TGCGGCTTGC  TGGTGACAAG
            CTCACCGCCT  GCCGGCAACG  CCTCCAGCGG
GAGAAATACC  AGCGTCGTGG  TTTAAGCCAG
            GATCCGTTGT  ATAAAAACCG  GAAGACCTTG
TTGACCACGC  ACAAGTGGTT  GAGTCCTCGT
            CAGCAAGAAA  GCTTGGAGCA  GTTGTGGGCG
TATGACAAAG  ACTACGGGGT  GTTAAAGCTT
            GCGTGGCTTG  CGTATCAGGC  GATTATTGAT
TGTTATCAGA  TGGGTAATAA  GCGTGAAGCG
            AAGAAGAAAA  TGCGGACCAT  TATTGATCAG
CTTCGGGTGT  TGAAGGGGCC  GAATAAGGAA
            CTCGCGCAGT  TGGGTCGTAG  TTTGTTTAAA
CGACTTGGTG  ATGTGTTGGC  GTATTTCGAC
            GTAGGAGTCT  CCAACGGACC  AGTCGAAGCC
ATCAATGGAC  GCCTAGAACA  CCTCCGCGGA
            ATCGCGCTTG  GATTCCGCAA  CCTCACCCAC
TACATCCTTC  GATGCCTCAT  CCACTCCGGA
            CAGCTCACCC  ACAAAATCAA  TGCACTCTAA
AAACGGAAG   AGCC.
```

2. A DNA fragment having insertion sequence activity and which transfers a DNA into the chromosomal DNA of a microorganism of the genus Brevibacterium or into a plasmid having a replication origin of said microorganism, said DNA fragment comprising:

(a) a gene coding for a transposase, a base sequence selected from the group consisting of the sequence of SEQ ID NO:5 and the sequence complementary to the reversed or inverted sequence of SEQ ID NO:6 or SEQ ID NO:7 located at one of the termini of said DNA fragment, and a base sequence selected from the group consisting of the sequence of SEQ ID NO:6, SEQ ID NO:7 and the sequence complementary to the reversed sequence of SEQ ID NO:5 located at the other terminus of said DNA fragment, or (b) a gene coding for a transposase, a base sequence selected from the group consisting of the sequence complementary to SEQ ID NO:5 and the reversed sequence of SEQ ID NO:6 or SEQ ID NO:7 at one of the termini of said DNA fragment, and a base sequence selected from the group consisting of the reversed sequence of SEQ ID NO:5 and the base sequence complementary to SEQ ID NO:6 or SEQ ID NO:7 at the other terminus of said DNA sequence.

3. The DNA fragment of claim 2, wherein said transposase comprises the amino acid sequence of SEQ ID NO:2.

4. The DNA fragment of claim 2, which comprises the nucleotide sequence of SEQ ID NO:1 or SEQ ID NO:3.

5. A DNA fragment having insertion sequence activity and which transfers a DNA into the chromosomal DNA of a microorganism of the genus Brevibacterium or into a plasmid having a replication origin of said microorganism, which comprises the nucleotide sequence of SEQ ID NO:4.

6. A DNA fragment or any of claims 2–4 or 5, which further comprises a replication origin of a microorganism of the genus Brevibacterium.

7. The DNA fragment of claim 6, wherein said replication origin is a temperature sensitive replication origin.

8. The DNA fragment of any of claims 2–4 or 5, which further comprises a selection marker gene, whereby a transposon-like sequence is formed.

9. The DNA fragment of claim 8, wherein said selection marker gene is a gene which confers resistance to an antibiotic on said strain.

10. The DNA fragment of any of claims 2–4 or 5, which is a plasmid or phage DNA which replicates in a microorganism of the genus Brevibacterium.

11. A microorganism of the genus Brevibacterium which comprises the DNA fragment of claim 8.

12. A process for transferring a DNA into the chromosomal DNA of a microorganism of the genus Brevibacterium or into a plasmid having a replication origin of said microorganism, which comprises incorporating into said chromosomal DNA of said microorganism the DNA fragment of claim 8.

13. The process of claim 12, wherein said microorganism contains a plasmid as a transfer target of a transposon-like sequence, is transformed with a DNA fragment comprising a temperature sensitive replication origin and a selection marker gene, and is cultured under a temperature at which the DNA fragment having a temperature sensitive replication origin does not replicate.

14. A process for obtaining the DNA fragment of claim 2 which comprises the steps of 1) introducing plasmid pEC701 into a strain belonging to the genus Brevibacterium to produce a strain transformed with pEC701, 2) selecting for said strain transformed with pEC701 using kanamycin resistance as a marker, 3) inoculating a said strain transformed with pEC701 onto an IPTG-containing agar plate to select a strain grown on the medium, 4) analyzing the nucleotide sequence of a CAT structural gene or expression regulating sequence of a plasmid contained in the selected strain, and 5) identifying a fragment comprising an insertion sequence inserted into said nucleotide sequence.

15. A process for obtaining the DNA fragment of claim 5 which comprises the steps of 1) introducing plasmid pEC901 into a strain belonging to the genus Brevibacterium to produce a strain transformed with pEC901
2) selecting for said strain transformed with pEC901 using kanamycin resistance as a marker,
3) culturing a said strain transformed with pEC901 at 30° C. to select a strain which expresses chloramphenicol resistance under a condition of 30° C.,
4) analyzing the nucleotide sequence of a cI repressor gene of a plasmid contained in the selected strain, and
5) identifying a fragment comprising an insertion sequence inserted into said nucleotide sequence.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
  ( A ) LENGTH: 1453 base pairs
  ( B ) TYPE: nucleic acid
  ( C ) STRANDEDNESS: double
  ( D ) TOPOLOGY: linear ( i i ) MOLECULE TYPE: DNA (genomic)

( v i ) ORIGINAL SOURCE:
  ( A ) ORGANISM: Brevibacterium lactofermentum
  ( B ) STRAIN: AJ2256

( i x ) FEATURE:
  ( A ) NAME/KEY: CDS
  ( B ) LOCATION: 130..1437

( x i ) SEQUENCE DESCRIPTION: SEQ ID NO:1:

```
GGCCCTTCCG GTTTTGGGGT ACATCACAGA ACCTGGGCTA GCGGTGTAGA CCCGAAAATA           60

AACGAGCCTT TTGTCAGGGT TAAGGTTTAG GTATCTAAGC TAACCAAACA CCAACAAAAG          120

GCTCTACCC ATG AAG TCT ACC GGC AAC ATC ATC GCT GAC ACC ATC TGC             168
          Met Lys Ser Thr Gly Asn Ile Ile Ala Asp Thr Ile Cys
           1               5                    10

CGC ACT GCG GAA CTA GGA CTC ACC ATC ACC GGC GCT TCC GAT GCA GGT           216
Arg Thr Ala Glu Leu Gly Leu Thr Ile Thr Gly Ala Ser Asp Ala Gly
     15              20                  25

GAT TAC ACC CTG ATC GAA GCA GAC GCA CTC GAC TAT ACC TCC ACC TGC           264
Asp Tyr Thr Leu Ile Glu Ala Asp Ala Leu Asp Tyr Thr Ser Thr Cys
 30              35                  40                      45

CCA GAA TGC TTC CAA CCT GGG GTG TTT CGT CAT CAC ACC CAC CGG ATG           312
Pro Glu Cys Phe Gln Pro Gly Val Phe Arg His His Thr His Arg Met
                 50                  55                  60

CTC ATT GAT TTA CCC ATC GTC GGG TTT CCC ACC AAA CTG TTT ATC CGT           360
Leu Ile Asp Leu Pro Ile Val Gly Phe Pro Thr Lys Leu Phe Ile Arg
             65                  70                  75

CTA CCT CGC TAC CGC TGC ACC AAC CCG ACA TGT AAG CAA AAG TAT TTC           408
Leu Pro Arg Tyr Arg Cys Thr Asn Pro Thr Cys Lys Gln Lys Tyr Phe
         80                  85                  90

CAA GCA GAA CTA AGC TGC GCT GAC CAC GGT AAA AAG GTC ACC CAC CGG           456
Gln Ala Glu Leu Ser Cys Ala Asp His Gly Lys Lys Val Thr His Arg
     95                 100                 105

GTC ACC CGC TGG ATT TTG CAA CGC CTT GCT ATT GAC CGG ATG AGT GTT           504
Val Thr Arg Trp Ile Leu Gln Arg Leu Ala Ile Asp Arg Met Ser Val
110                 115                 120                 125

CAC GCA ACT GCG AAA GCA CTT GGG CTA GGG TGG GAT TTA ACC TGC CAA           552
His Ala Thr Ala Lys Ala Leu Gly Leu Gly Trp Asp Leu Thr Cys Gln
                130                 135                 140

CTA GCC CTC GAT ATG TGC CGT GAG CTG GTC TAT AAC GAT CCT CAC CAT           600
Leu Ala Leu Asp Met Cys Arg Glu Leu Val Tyr Asn Asp Pro His His
             145                 150                 155
```

| | | | | | | | | | | | | | | | | |
|---|---|---|---|---|---|---|---|---|---|---|---|---|---|---|---|---|
| CTT | GAT | GGA | GTG | TAT | GTC | ATT | GGG | GTG | GAT | GAG | CAT | AAG | TGG | TCA | CAT | 648 |
| Leu | Asp | Gly | Val | Tyr | Val | Ile | Gly | Val | Asp | Glu | His | Lys | Trp | Ser | His | |
| | | 160 | | | | 165 | | | | | 170 | | | | | |
| AAT | AGG | GCT | AAG | CAT | GGT | GAT | GGG | TTT | GTC | ACC | GTG | ATT | GTC | GAT | ATG | 696 |
| Asn | Arg | Ala | Lys | His | Gly | Asp | Gly | Phe | Val | Thr | Val | Ile | Val | Asp | Met | |
| | 175 | | | | | 180 | | | | | 185 | | | | | |
| ACC | GGG | CAT | CGG | TAT | GAC | TCA | CGG | TGT | CCT | GCC | CGG | TTA | TTA | GAT | GTC | 744 |
| Thr | Gly | His | Arg | Tyr | Asp | Ser | Arg | Cys | Pro | Ala | Arg | Leu | Leu | Asp | Val | |
| 190 | | | | | 195 | | | | | 200 | | | | | 205 | |
| GTC | CCA | GGT | CGT | AGT | GCT | GAT | GCT | TTA | CGG | TCC | TGG | CTT | GGC | TCC | CGC | 792 |
| Val | Pro | Gly | Arg | Ser | Ala | Asp | Ala | Leu | Arg | Ser | Trp | Leu | Gly | Ser | Arg | |
| | | | | 210 | | | | | 215 | | | | | 220 | | |
| GGT | GAA | CAG | TTC | CGC | AAT | CAG | ATA | CGG | ATC | GTG | TCC | ATG | GAT | GGA | TTC | 840 |
| Gly | Glu | Gln | Phe | Arg | Asn | Gln | Ile | Arg | Ile | Val | Ser | Met | Asp | Gly | Phe | |
| | | | 225 | | | | | 230 | | | | | 235 | | | |
| CAA | GGC | TAC | GCC | ACA | GCA | AGT | AAA | GAA | CTC | ATT | CCT | TCT | GCT | CGT | CGC | 888 |
| Gln | Gly | Tyr | Ala | Thr | Ala | Ser | Lys | Glu | Leu | Ile | Pro | Ser | Ala | Arg | Arg | |
| | | 240 | | | | | 245 | | | | | 250 | | | | |
| GTG | ATG | GAT | CCA | TTC | CAT | GTT | GTG | CGG | CTT | GCT | GGT | GAC | AAG | CTC | ACC | 936 |
| Val | Met | Asp | Pro | Phe | His | Val | Val | Arg | Leu | Ala | Gly | Asp | Lys | Leu | Thr | |
| | 255 | | | | | 260 | | | | | 265 | | | | | |
| GCC | TGC | CGG | CAA | CGC | CTC | CAG | CGG | GAG | AAA | TAC | CAG | CGT | CGT | GGT | TTA | 984 |
| Ala | Cys | Arg | Gln | Arg | Leu | Gln | Arg | Glu | Lys | Tyr | Gln | Arg | Arg | Gly | Leu | |
| 270 | | | | | 275 | | | | | 280 | | | | | 285 | |
| AGC | CAG | GAT | CCG | TTG | TAT | AAA | AAC | CGG | AAG | ACC | TTG | TTG | ACC | ACG | CAC | 1032 |
| Ser | Gln | Asp | Pro | Leu | Tyr | Lys | Asn | Arg | Lys | Thr | Leu | Leu | Thr | Thr | His | |
| | | | | 290 | | | | | 295 | | | | | | 300 | |
| AAG | TGG | TTG | AGT | CCT | CGT | CAG | CAA | GAA | AGC | TTG | GAG | CAG | TTG | TGG | GCG | 1080 |
| Lys | Trp | Leu | Ser | Pro | Arg | Gln | Gln | Glu | Ser | Leu | Glu | Gln | Leu | Trp | Ala | |
| | | | 305 | | | | | 310 | | | | | 315 | | | |
| TAT | GAC | AAA | GAC | TAC | GGG | GTG | TTA | AAG | CTT | GCG | TGG | CTT | GCG | TAT | CAG | 1128 |
| Tyr | Asp | Lys | Asp | Tyr | Gly | Val | Leu | Lys | Leu | Ala | Trp | Leu | Ala | Tyr | Gln | |
| | | 320 | | | | | 325 | | | | | 330 | | | | |
| GCG | ATT | ATT | GAT | TGT | TAT | CAG | ATG | GGT | AAT | AAG | CGT | GAA | GCG | AAG | AAG | 1176 |
| Ala | Ile | Ile | Asp | Cys | Tyr | Gln | Met | Gly | Asn | Lys | Arg | Glu | Ala | Lys | Lys | |
| | 335 | | | | | 340 | | | | | 345 | | | | | |
| AAA | ATG | CGG | ACC | ATT | ATT | GAT | CAG | CTT | CGG | GTG | TTG | AAG | GGG | CCG | AAT | 1224 |
| Lys | Met | Arg | Thr | Ile | Ile | Asp | Gln | Leu | Arg | Val | Leu | Lys | Gly | Pro | Asn | |
| 350 | | | | | 355 | | | | | 360 | | | | | 365 | |
| AAG | GAA | CTC | GCG | CAG | TTG | GGT | CGT | AGT | TTG | TTT | AAA | CGA | CTT | GGT | GAT | 1272 |
| Lys | Glu | Leu | Ala | Gln | Leu | Gly | Arg | Ser | Leu | Phe | Lys | Arg | Leu | Gly | Asp | |
| | | | | 370 | | | | | 375 | | | | | 380 | | |
| GTG | TTG | GCG | TAT | TTC | GAC | GTA | GGA | GTC | TCC | AAC | GGA | CCA | GTC | GAA | GCC | 1320 |
| Val | Leu | Ala | Tyr | Phe | Asp | Val | Gly | Val | Ser | Asn | Gly | Pro | Val | Glu | Ala | |
| | | | 385 | | | | | 390 | | | | | 395 | | | |
| ATC | AAT | GGA | CGC | CTA | GAA | CAC | CTC | CGC | GGA | ATC | GCG | CTT | GGA | TTC | CGC | 1368 |
| Ile | Asn | Gly | Arg | Leu | Glu | His | Leu | Arg | Gly | Ile | Ala | Leu | Gly | Phe | Arg | |
| | | 400 | | | | | 405 | | | | | 410 | | | | |
| AAC | CTC | ACC | CAC | TAC | ATC | CTT | CGA | TGC | CTC | ATC | CAC | TCC | GGA | CAG | CTC | 1416 |
| Asn | Leu | Thr | His | Tyr | Ile | Leu | Arg | Cys | Leu | Ile | His | Ser | Gly | Gln | Leu | |
| | 415 | | | | | 420 | | | | | 425 | | | | | |
| ACC | CAC | AAA | ATC | AAT | GCA | CTC | TAAAAACGGA | AGAGCC | | | | | | | | 1453 |
| Thr | His | Lys | Ile | Asn | Ala | Leu | | | | | | | | | | |
| 430 | | | | | 435 | | | | | | | | | | | |

( 2 ) INFORMATION FOR SEQ ID NO:2:

( i ) SEQUENCE CHARACTERISTICS:
        ( A ) LENGTH: 436 amino acids
        ( B ) TYPE: amino acid
        ( D ) TOPOLOGY: linear (ii) MOLECULE TYPE: protein (xi) SEQUENCE DESCRIPTION: SEQ ID NO:2:

| Met | Lys | Ser | Thr | Gly | Asn | Ile | Ile | Ala | Asp | Thr | Ile | Cys | Arg | Thr | Ala |
|---|---|---|---|---|---|---|---|---|---|---|---|---|---|---|---|
| 1 | | | | 5 | | | | | 10 | | | | | 15 | |

| Glu | Leu | Gly | Leu | Thr | Ile | Thr | Gly | Ala | Ser | Asp | Ala | Gly | Asp | Tyr | Thr |
|---|---|---|---|---|---|---|---|---|---|---|---|---|---|---|---|
| | | | 20 | | | | | 25 | | | | | 30 | | |

| Leu | Ile | Glu | Ala | Asp | Ala | Leu | Asp | Tyr | Thr | Ser | Thr | Cys | Pro | Glu | Cys |
|---|---|---|---|---|---|---|---|---|---|---|---|---|---|---|---|
| | | | 35 | | | | 40 | | | | | 45 | | | |

| Phe | Gln | Pro | Gly | Val | Phe | Arg | His | His | Thr | His | Arg | Met | Leu | Ile | Asp |
|---|---|---|---|---|---|---|---|---|---|---|---|---|---|---|---|
| | 50 | | | | | 55 | | | | | 60 | | | | |

| Leu | Pro | Ile | Val | Gly | Phe | Pro | Thr | Lys | Leu | Phe | Ile | Arg | Leu | Pro | Arg |
|---|---|---|---|---|---|---|---|---|---|---|---|---|---|---|---|
| 65 | | | | | 70 | | | | | 75 | | | | | 80 |

| Tyr | Arg | Cys | Thr | Asn | Pro | Thr | Cys | Lys | Gln | Lys | Tyr | Phe | Gln | Ala | Glu |
|---|---|---|---|---|---|---|---|---|---|---|---|---|---|---|---|
| | | | | 85 | | | | | 90 | | | | | 95 | |

| Leu | Ser | Cys | Ala | Asp | His | Gly | Lys | Lys | Val | Thr | His | Arg | Val | Thr | Arg |
|---|---|---|---|---|---|---|---|---|---|---|---|---|---|---|---|
| | | | 100 | | | | | 105 | | | | | 110 | | |

| Trp | Ile | Leu | Gln | Arg | Leu | Ala | Ile | Asp | Arg | Met | Ser | Val | His | Ala | Thr |
|---|---|---|---|---|---|---|---|---|---|---|---|---|---|---|---|
| | | | 115 | | | | | 120 | | | | | 125 | | |

| Ala | Lys | Ala | Leu | Gly | Leu | Gly | Trp | Asp | Leu | Thr | Cys | Gln | Leu | Ala | Leu |
|---|---|---|---|---|---|---|---|---|---|---|---|---|---|---|---|
| | 130 | | | | | 135 | | | | | 140 | | | | |

| Asp | Met | Cys | Arg | Glu | Leu | Val | Tyr | Asn | Asp | Pro | His | His | Leu | Asp | Gly |
|---|---|---|---|---|---|---|---|---|---|---|---|---|---|---|---|
| 145 | | | | | 150 | | | | | 155 | | | | | 160 |

| Val | Tyr | Val | Ile | Gly | Val | Asp | Glu | His | Lys | Trp | Ser | His | Asn | Arg | Ala |
|---|---|---|---|---|---|---|---|---|---|---|---|---|---|---|---|
| | | | | 165 | | | | | 170 | | | | | 175 | |

| Lys | His | Gly | Asp | Gly | Phe | Val | Thr | Val | Ile | Val | Asp | Met | Thr | Gly | His |
|---|---|---|---|---|---|---|---|---|---|---|---|---|---|---|---|
| | | | 180 | | | | | 185 | | | | | 190 | | |

| Arg | Tyr | Asp | Ser | Arg | Cys | Pro | Ala | Arg | Leu | Leu | Asp | Val | Val | Pro | Gly |
|---|---|---|---|---|---|---|---|---|---|---|---|---|---|---|---|
| | | 195 | | | | | 200 | | | | | 205 | | | |

| Arg | Ser | Ala | Asp | Ala | Leu | Arg | Ser | Trp | Leu | Gly | Ser | Arg | Gly | Glu | Gln |
|---|---|---|---|---|---|---|---|---|---|---|---|---|---|---|---|
| | 210 | | | | | 215 | | | | | 220 | | | | |

| Phe | Arg | Asn | Gln | Ile | Arg | Ile | Val | Ser | Met | Asp | Gly | Phe | Gln | Gly | Tyr |
|---|---|---|---|---|---|---|---|---|---|---|---|---|---|---|---|
| 225 | | | | | 230 | | | | | 235 | | | | | 240 |

| Ala | Thr | Ala | Ser | Lys | Glu | Leu | Ile | Pro | Ser | Ala | Arg | Arg | Val | Met | Asp |
|---|---|---|---|---|---|---|---|---|---|---|---|---|---|---|---|
| | | | | 245 | | | | | 250 | | | | | 255 | |

| Pro | Phe | His | Val | Val | Arg | Leu | Ala | Gly | Asp | Lys | Leu | Thr | Ala | Cys | Arg |
|---|---|---|---|---|---|---|---|---|---|---|---|---|---|---|---|
| | | | 260 | | | | | 265 | | | | | 270 | | |

| Gln | Arg | Leu | Gln | Arg | Glu | Lys | Tyr | Gln | Arg | Arg | Gly | Leu | Ser | Gln | Asp |
|---|---|---|---|---|---|---|---|---|---|---|---|---|---|---|---|
| | | 275 | | | | | 280 | | | | | 285 | | | |

| Pro | Leu | Tyr | Lys | Asn | Arg | Lys | Thr | Leu | Leu | Thr | Thr | His | Lys | Trp | Leu |
|---|---|---|---|---|---|---|---|---|---|---|---|---|---|---|---|
| | 290 | | | | | 295 | | | | | 300 | | | | |

| Ser | Pro | Arg | Gln | Gln | Glu | Ser | Leu | Glu | Gln | Leu | Trp | Ala | Tyr | Asp | Lys |
|---|---|---|---|---|---|---|---|---|---|---|---|---|---|---|---|
| 305 | | | | | 310 | | | | | 315 | | | | | 320 |

| Asp | Tyr | Gly | Val | Leu | Lys | Leu | Ala | Trp | Leu | Ala | Tyr | Gln | Ala | Ile | Ile |
|---|---|---|---|---|---|---|---|---|---|---|---|---|---|---|---|
| | | | | 325 | | | | | 330 | | | | | 335 | |

| Asp | Cys | Tyr | Gln | Met | Gly | Asn | Lys | Arg | Glu | Ala | Lys | Lys | Lys | Met | Arg |
|---|---|---|---|---|---|---|---|---|---|---|---|---|---|---|---|
| | | | 340 | | | | | 345 | | | | | 350 | | |

| Thr | Ile | Ile | Asp | Gln | Leu | Arg | Val | Leu | Lys | Gly | Pro | Asn | Lys | Glu | Leu |
|---|---|---|---|---|---|---|---|---|---|---|---|---|---|---|---|
| | | 355 | | | | | 360 | | | | | 365 | | | |

| Ala | Gln | Leu | Gly | Arg | Ser | Leu | Phe | Lys | Arg | Leu | Gly | Asp | Val | Leu | Ala |
|---|---|---|---|---|---|---|---|---|---|---|---|---|---|---|---|
| | 370 | | | | | 375 | | | | | 380 | | | | |

| Tyr | Phe | Asp | Val | Gly | Val | Ser | Asn | Gly | Pro | Val | Glu | Ala | Ile | Asn | Gly |
|---|---|---|---|---|---|---|---|---|---|---|---|---|---|---|---|
| 385 | | | | | 390 | | | | | 395 | | | | | 400 |

| Arg | Leu | Glu | His | Leu | Arg | Gly | Ile | Ala | Leu | Gly | Phe | Arg | Asn | Leu | Thr |

| | 405 | | 410 | | 415 | |
|---|---|---|---|---|---|---|
His Tyr Ile Leu Arg Cys Leu Ile His Ser Gly Gln Leu Thr His Lys
                420                 425                 430

Ile Asn Ala Leu
         435

( 2 ) INFORMATION FOR SEQ ID NO:3:

( i ) SEQUENCE CHARACTERISTICS:
        ( A ) LENGTH: 1441 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Brevibacterium lactofermentum
        ( B ) STRAIN: AJ2256

( i x ) FEATURE:
        ( A ) NAME/KEY: insertion_seq
        ( B ) LOCATION: 1..1141

( x i ) SEQUENCE DESCRIPTION: SEQ ID NO:3:

| | | | | | | |
|---|---|---|---|---|---|---|
| GGCCCTTCCG | GTTTTGGGGT | ACATCACAGA | ACCTGGGCTA | GCGGTGTAGA | CCCGAAAATA | 60 |
| AACCGGAGCC | CTTTTGTCAG | GGTTAAGGTT | TAGGTATCTA | AGCTAACCAA | ACACCAACAA | 120 |
| AGGCTCTACC | ATGAAGTCTA | CCGGCAACAT | CATCGCTGAC | ACCATCTGCC | GCACTGCGAA | 180 |
| CTAGGACTCA | CCATCACCGG | GGCTTCCGAT | GCAGGTGATT | ACACCTGATC | GAAGCAGACG | 240 |
| CACTCGACTA | TACCTCCACC | TGCCCAGAAT | GCTTCCAACC | TGGGGTGTTT | CGTCATCACA | 300 |
| CCCACCGGAT | GCTCATTGAT | TTACCCATCG | TCGGGTTTCC | ACCAAACTGT | TTATCCGTCT | 360 |
| ACCTCGCTAC | CGCTGCACCA | ACCCGACATG | TAAGCAAAAG | TATTTCCAAG | CAGAACTAAG | 420 |
| CTGCGCTGAC | CACGGTAAAA | AGGTCACCCA | CCGGTCACCC | GCTGGATTTT | GCAACGCCTT | 480 |
| GCTATTGACC | GGATGAGTGT | TCACGCAACT | GCGAAAGCAC | TTGGGCTAGG | GTGGGATTTA | 540 |
| ACCTGCCAAC | TAGCCCTCGA | TATGTGCCGT | GAGCTGGTCT | ATAACGATCC | TCACCATCTT | 600 |
| GATGGAGTGT | ATGTCATTGG | GGTGGATGAG | CATAAGTGGT | CACATAATAG | GCTAAGCAT | 660 |
| GGTGATGGGT | TTGTCACCGT | GATTGTCGAT | ATGACCGGGC | ATCGTATGAC | TCACGTGTCT | 720 |
| GCCGGTTATT | AGATGTCGTC | CCAGGTCGTA | GTGCTGATGC | TTTACGGTCC | TGGCTTGGCT | 780 |
| CCCGCGGTGA | ACAGTTCCGC | AATCAGATAC | GGATCGTGTC | CATGGATGGA | TTCCAATACG | 840 |
| CCACAGCAAG | TAAAGAACTC | ATTCCTTCTG | CTCGTCGCGT | GATGGATCCA | TTCCATGTTG | 900 |
| TGCGGCTTGC | TGGTGACAAG | CTCACGCCTG | CGGCAACGCC | TCCAGCGGGA | GAAATACCAG | 960 |
| CGTCGTGGTT | TAAGCCAGGA | TCCGTTGTAT | AAAAACCGGA | AGACCTTGTT | GACCACGCAC | 1020 |
| AAGTGGTTGA | GTCCTCGTCA | GCAAGAAAGC | TTGGAGCAGT | TGTGGCGTAT | GACAAAGACT | 1080 |
| ACGGGGTGTT | AAAGCTTGCG | TGGCTTGCGT | ATCAGGCGAT | TATTGATTGT | TATCAGATGG | 1140 |
| GTAATAAGCG | TGAAGCGAAG | AAGAAAATGC | GGACCATTAT | TGATCAGCTT | CGGGTGTTGA | 1200 |
| AGGGCCGAAT | AAGGAACTCG | CGCAGTTGGG | TCGTAGTTTG | TTTAAACGAC | TTGGTGATGT | 1260 |
| GTTGGCGTAT | TTCGATGTTG | GTGTCTCCAA | CGGTCCGGTC | GAAGCGATCA | ACGGACGGTT | 1320 |
| GGAGCATTTG | CGTGGGATTG | CTCTAGGTTT | CCGTAATTTG | AACCACCTAC | ATTCTGCGGT | 1380 |
| GCCTTATCCA | TTCAGGGCAG | TTGGTCCATA | AGATCAATGC | ACTCTAAAAC | AGGAAGAGCC | 1440 |
| C | | | | | | 1441 |

( 2 ) INFORMATION FOR SEQ ID NO:4:

( i ) SEQUENCE CHARACTERISTICS:
        ( A ) LENGTH: 1279 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Brevibacterium lactofermentum
        ( B ) STRAIN: AJ2256

( i x ) FEATURE:
        ( A ) NAME/KEY: insertion_seq
        ( B ) LOCATION: 1..1279

( x i ) SEQUENCE DESCRIPTION: SEQ ID NO:4:

| | | | | | | |
|---|---|---|---|---|---|---|
| GGGACTGACC | CCTGTTTGGT | GGACACCTTG | AAACCAGCAT | GATGCTGGAA | AGGTAATCTG | 60 |
| CCACCATGCC | ACGCAAGACC | TATACAGAGG | AGTTCAAGCG | CGATGCCGTC | GCCTTGTACG | 120 |
| AGAACTCCCC | AGAGGCTTCG | ATCCAGACCA | TCGCCACCGA | TCTCGGGGTC | AACCGCGCCA | 180 |
| CGTTGGCGAA | CTGGGTGAAA | AAATACGGCA | CCGCAGGCTC | CCAACGAAAC | ACCCTCGCCA | 240 |
| GCCTCTGTGA | ACGAGGCTGA | GCAGATCCGG | AAACTGGAAC | GGGAAAACGC | TCGCTTGAGA | 300 |
| GAAGAGCGCG | ATATCCTGCG | GAAAGCTGCA | AAATATTTCG | CGGAAGAGAC | GAATTGGTGA | 360 |
| TCCGCTTCCG | GTTCGTTGAT | GACGCCTCCA | AGACCTACTC | GGTCAAGCGG | ATATGTGACG | 420 |
| TCCTCAAACT | CAACAGGTCT | TCCTACTATA | AATGGAAAAG | TACCTGCTCA | GCACGCAGGA | 480 |
| AACGCCTCAT | GTCGACGCGA | TCCTCGGGGC | TCGAGTCAAG | GCTGTCTTCA | CCACCGAAAA | 540 |
| TGGTTGTTAT | GGGGCCAAGC | GGATCACCGC | TGAACTCAAA | GACCAGGTGG | ATCATGACCC | 600 |
| CGTAAATCAC | AAGCGGGTCG | CTCGGGTGAT | GCGCTCGTTG | AAGCTGTTTG | GCTACACAAA | 660 |
| TAAACGCAAG | GTCACCACCA | CTGTGTCGGA | TAAAACCAAG | ACAGTGTTTC | CTGACCTTGT | 720 |
| CGGCCGGAAG | TTCACCGCTA | ATAAGCCAAA | TCAGGTGTAC | GTCGGGACAT | CACGTACCTG | 780 |
| CCGATTGCTG | ATGGGTCGAA | TATGTACCTG | GCTACGGTCA | TTGACTGCTA | TTCCCGCAGG | 840 |
| TTGGTGGGCT | TTTCTATCGC | ACATCACATG | CGTACCTCCC | TGGTGCAGAC | GCGCTGCTGA | 900 |
| TGGCTAAGGG | CCAGCGCGAA | GCTGACGGGG | GCGATCTTTC | ACTCGGATCA | CGGAAGTGTT | 960 |
| TACACTTCTC | ACGCATTCCA | GACACCTGTA | AAGACCTGGG | ATAAGGCAGT | CGATGGGATC | 1020 |
| AATCGGCACC | AGTGCGACAA | TGCCTCGCGG | AGTCCTTCAA | CGCAGCACTG | AAGCGGAAGT | 1080 |
| CCTCCAGGAT | TCCAAGACAT | TCATGAACCA | GTTGCGCTGT | CGCCGGGACG | TCTTCCGCTG | 1140 |
| GTGTACCCGC | TACAACATGG | TGCGCCGGCA | TTCCTGGTGT | AAATATCTCG | CCCTGCGGTG | 1200 |
| TTTGAGAAGC | GCTGTCCTGC | TATCCTGAAA | TCTGCTTCCT | GATCAAATCC | TCCGTGTCTA | 1260 |
| CTATCCGGGG | GTCGGGCCC | | | | | 1279 |

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( A ) ORGANISM: Brevibacterium lactofermentum
        ( B ) STRAIN: AJ2256

( x i ) SEQUENCE DESCRIPTION: SEQ ID NO:5:

GGCCCTTCCG GTTTT  15

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Brevibacterium lactofermentum
        (B) STRAIN: AJ2256

(xi) SEQUENCE DESCRIPTION: SEQ ID NO:6:

AAAAACGGAA GAGCC  15

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Brevibacterium lactofermentum
        (B) STRAIN: AJ2256

(xi) SEQUENCE DESCRIPTION: SEQ ID NO:7:

AAAACAGGAA GAGCC  15

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Brevibacterium lactofermentum
        (B) STRAIN: AJ2256

(xi) SEQUENCE DESCRIPTION: SEQ ID NO:8:

GGGACTGACC CCTG  14

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Brevibacterium lactofermentum
        (B) STRAIN: AJ2256

(xi) SEQUENCE DESCRIPTION: SEQ ID NO:9:

CGGGGGTCGG GCCC  14